(12) United States Patent
Blamey et al.

(10) Patent No.: US 8,260,429 B2
(45) Date of Patent: Sep. 4, 2012

(54) INCREMENTAL STIMULATION SOUND PROCESSOR

(75) Inventors: Peter J. Blamey, South Yarra (AU); Bonar Dickson, Abbotsford (AU); Brett A. Swanson, St. Ives (AU)

(73) Assignees: The University of Melbourne, Melbourne, Victoria (AU); Bionic Ear Institute, Melbourne, Victoria (AU); Cochlear Limited, Macquarie University, NSW (AU)

( * ) Notice: Subject to any disclaimer, the term of this patent is extended or adjusted under 35 U.S.C. 154(b) by 624 days.

(21) Appl. No.: 12/013,249

(22) Filed: Jan. 11, 2008

(65) Prior Publication Data
US 2009/0018615 A1    Jan. 15, 2009

Related U.S. Application Data

(63) Continuation of application No. 11/066,999, filed on Feb. 28, 2005, now Pat. No. 7,321,797.

(51) Int. Cl.
*A61N 1/36* (2006.01)

(52) U.S. Cl. .......................... 607/57; 607/56

(58) Field of Classification Search .............. 607/55–57, 607/59, 62, 66, 68, 137
See application file for complete search history.

(56) References Cited

U.S. PATENT DOCUMENTS

| | | | |
|---|---|---|---|
| 6,157,861 A * | 12/2000 | Faltys et al. ............ | 607/57 |
| 7,206,640 B1 | 4/2007 | Overstreet | |
| 2003/0171786 A1 | 9/2003 | Blamey et al. | |
| 2005/0107844 A1 | 5/2005 | Van Den Honert et al. | |
| 2005/0192646 A1 | 9/2005 | Grayden et al. | |

\* cited by examiner

*Primary Examiner* — Brian T Gedeon
(74) *Attorney, Agent, or Firm* — Kilpatrick, Townsend & Stockton, LLP.

(57) ABSTRACT

In one aspect of the invention, a cochlear implant constructed and arranged to successively generate stimulation signals each comprising at least one stimulus pulse such that said successive stimulation signals incrementally build a neural excitation pattern that accurately reflects a received sound. In one embodiment, each said successive stimulation signal is generated based on the cumulative effect of all previous stimulus pulses, thereby compensating for finite spatial spreading of individual stimulus pulses as well as for the temporal integration of the neural excitation pattern along the neural pathways.

32 Claims, 10 Drawing Sheets

INCREMENTAL STIMULATION SOUND PROCESSOR

CROSS-REFERENCE TO RELATED APPLICATIONS

This application is a continuation of U.S. patent application Ser. No. 11/066,999, now U.S. Pat. No. 7,321,797, filed Feb. 28, 2005, which is hereby incorporated by reference herein.

BACKGROUND

1. Field of the Invention

The present invention relates generally to hearing prostheses and, more particularly, to cochlear implant systems.

2. Related Art

The use of patient-worn and implantable medical devices to provide therapy to individuals for various medical conditions has become more widespread as the advantages and benefits such devices provide become more widely appreciated and accepted throughout the population. In particular, devices such as hearing aids, implantable pacemakers, defibrillators, functional electrical stimulation devices such as Cochlear™ implant systems, organ assist or replacement devices, and other medical devices, have been successful in performing life saving and/or lifestyle enhancement functions for a number of individuals.

One category of such medical devices is hearing prostheses which include but are not limited to hearing aids and Cochlear™ implant systems. Hearing aids are externally-worn devices which amplify sound to assist recipients who have degraded or impaired hearing due to, for example, age, injury or chronic ear or mastoid infections. Cochlear™ implant systems provide the benefit of hearing to individuals suffering from severe to profound hearing loss. Hearing loss in such individuals is due to the absence or destruction of the hair cells in the cochlea which transduce acoustic signals into nerve impulses. Cochlear™ implant systems essentially simulate the cochlear hair cells by directly delivering electrical stimulation to the auditory nerve fibers. This causes the brain to perceive a hearing sensation resembling the natural hearing sensation normally delivered to auditory nerves.

Conventional Cochlear™ implant systems have generally included an external assembly directly or indirectly attached to the body of the patient (sometimes referred to herein as the recipient), and an internal assembly which is implanted in the patient. More recently, some Cochlear™ implant systems have been designed such that all of the systems' components are implanted subcutaneously; that is there is no external assembly. Because such Cochlear™ implant systems are entirely implantable, they are commonly referred to as a "totally" implantable Cochlear™ implant.

Cochlear™ implant systems generally comprise a microphone for detecting sounds and a speech processor that converts the detected sounds into a coded signal provided to a stimulator unit which drives an electrode array implanted in the cochlea of the patient. The coded signals are applied by the electrode array to the basilar membrane thereby stimulating the auditory nerve.

A cochlear implant speech processor should be able to calculate an ideal neural excitation pattern, and then produce that pattern in the auditory neurons by activating the electrodes with appropriate electric current levels or charges per pulse. Specifically, the objective of pulsatile electrical encoding for cochlear implants is to convert an ideal spatio-temporal pattern of excitation (referred to herein as an ideal excitation pattern) to a sequence of variable biphasic stimulus pulses (referred to herein as a stimulation signal) that will best create the same pattern when presented on the implanted electrodes. The exact nature of excitation and its distribution in the cochlear and auditory pathway is open to debate, but the generally-accepted approach to quantify excitation is loudness.

The essential requirement of the encoding task is to recreate the ideal excitation pattern with as little error and reduction of information as possible, while minimizing perceptual artifacts from the pulsatile nature of the stimulation. With recent interest in patterns of excitation with greater temporal information, the effects of summation of loudness, and in the importance of technical improvements such as higher rates & more electrodes, it is useful to consider current encoding methods, and make improvements where possible.

SUMMARY

In one aspect of the invention, a cochlear implant is disclosed. The cochlear implant is constructed and arranged to successively generate stimulation signals each comprising at least one stimulus pulse such that said successive stimulation signals incrementally build a neural excitation pattern that accurately reflects a received sound. In one embodiment of this aspect of the invention, each said successive stimulation signal is generated based on the cumulative effect of all previous stimulus pulses, thereby compensating for finite spatial spreading of individual stimulus pulses as well as for the temporal integration of the neural excitation pattern along the neural pathways.

In another aspect of the invention, a speech processor of a cochlear implant is disclosed. The speech processor comprises: an incremental encoder constructed and arranged to generate stimulation pulses that incrementally build a neural excitation pattern that accurately reflects a received sound, wherein said incremental encoder comprises: an excitation model that maintains and updates an model current excitation pattern that takes into account the cumulative effect of all previously presented stimulus pulses presented at each electrode position; means for subtracting said model current excitation pattern from an ideal excitation pattern to generate an excitation error; and an error reducer constructed and arranged to use said excitation error to generate an electrical stimulus pattern to make up an incremental difference in said excitation pattern.

DETAILED DESCRIPTION

Figure 1A:
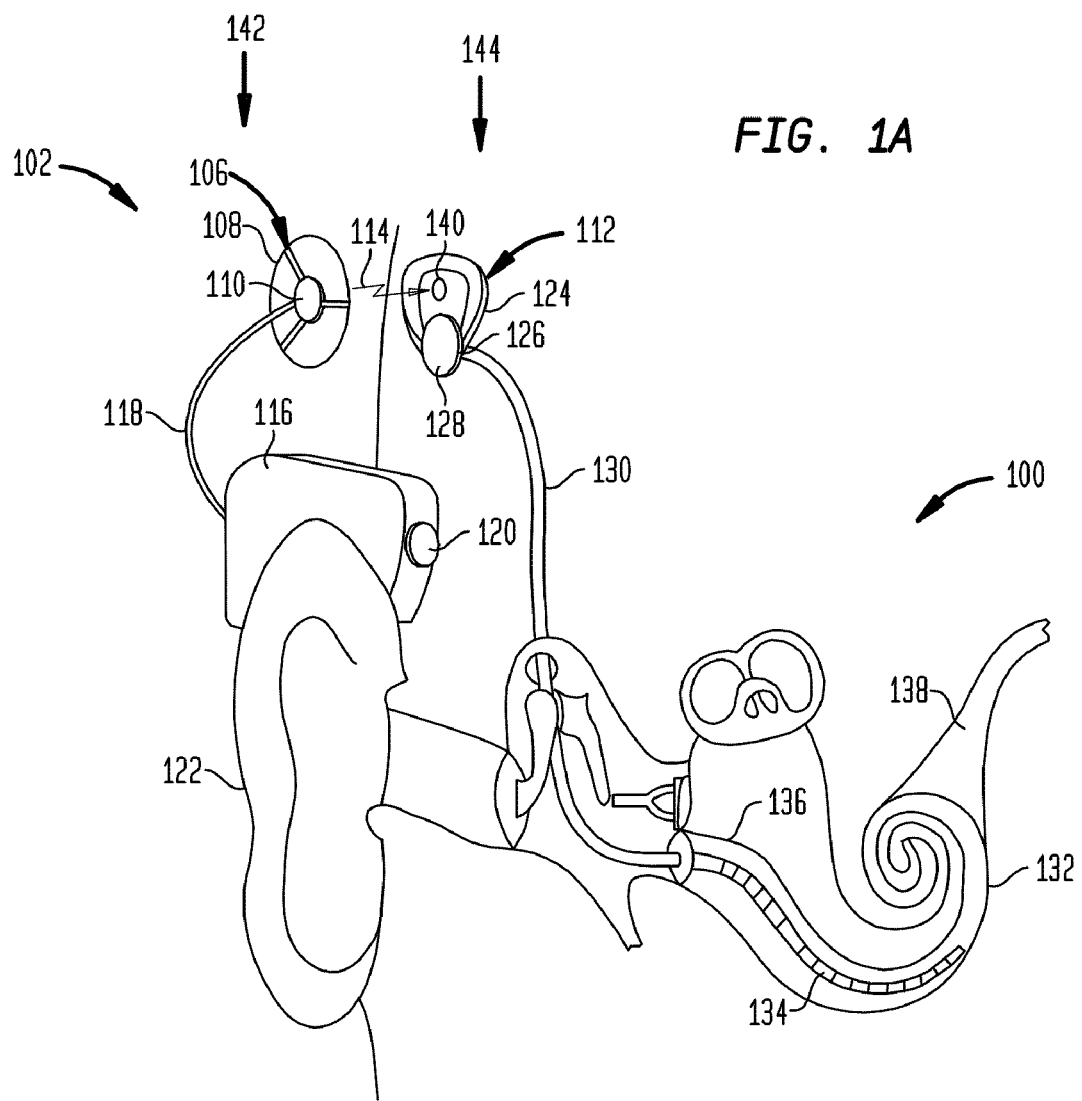
FIG. 1A is a schematic block diagram of one embodiment of an exemplary hearing prosthesis, specifically, a cochlear implant system, suitable for implementing embodiments of the present invention.

Aspects of the present invention are directed to the generation of stimulation pulses in a cochlear implant that incrementally builds a neural excitation pattern that accurately reflects a received sound. By taking into account the cumulative effect of previously-applied stimulus pulses, the present invention inherently compensates for the spatial spreading of excitation to adjacent electrodes, as well as for the temporal integration that may occur along the neural pathways.

Embodiments of the present invention are described below in connection with one embodiment of an exemplary implantable medical device, a hearing prosthesis. Specifically, the exemplary application is a Cochlear™ implant system (also referred to as a Cochlear™ prosthesis, Cochlear™ prosthetic device and the like; "cochlear implant" herein). Cochlear implants use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a cochlear implant provides stimulation of the cochlear nucleus in the brainstem.

Exemplary cochlear implants in which the present invention may be implemented include, but are not limited to, those systems described in U.S. Pat. Nos. 4,532,930, 6,537,200, 6,565,503, 6,575,894 and 6,697,674, which are hereby incorporated by reference herein. FIG. 1 is a schematic diagram of an exemplary cochlear implant system 100 in which embodiments of the present invention may be implemented. Cochlear implant system 100 comprises external components 142 which are directly or indirectly attached to the body of the recipient, and internal components 144 which are temporarily or permanently implanted in the recipient. External components 142 typically comprise a microphone 120 for detecting sounds, a speech processor 116 that converts the detected sounds into a coded stimulation signal, a power source (not shown), and an external transmitter unit 106. External transmitter unit 106 comprises an external coil 108 and a magnet 110 secured directly or indirectly to external coil 108. Speech processor 116 processes the output of microphone 120 that is positioned, in the depicted embodiment, on the ear 122 of the recipient. Speech processor 116 generates a coded stimulation signal which is provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to the basilar membrane 136 thereby stimulating the auditory nerve 138.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone molding (not shown). In use, implantable receiver unit 112 can be positioned in a recess of the temporal bone adjacent ear 122 of the recipient.

Implantable receiver unit 112 has a magnet 140 embedded within the silicone housing of internal coil 124 to allow transcutaneous alignment of external coil 108 of external transmitter unit 106 and internal coil 124 of internal receiver unit 112. This magnetic transcutaneous alignment provides an attraction force that is designed to maintain external coil 108 in place on the head of the recipient without the necessity for any additional clips or other holding means. This magnetic transcutaneous alignment also facilitates the correct lateral alignment of external coil 108 over internal coil 124 to permit the efficient transmission of power and/or data.

Figure 1B:
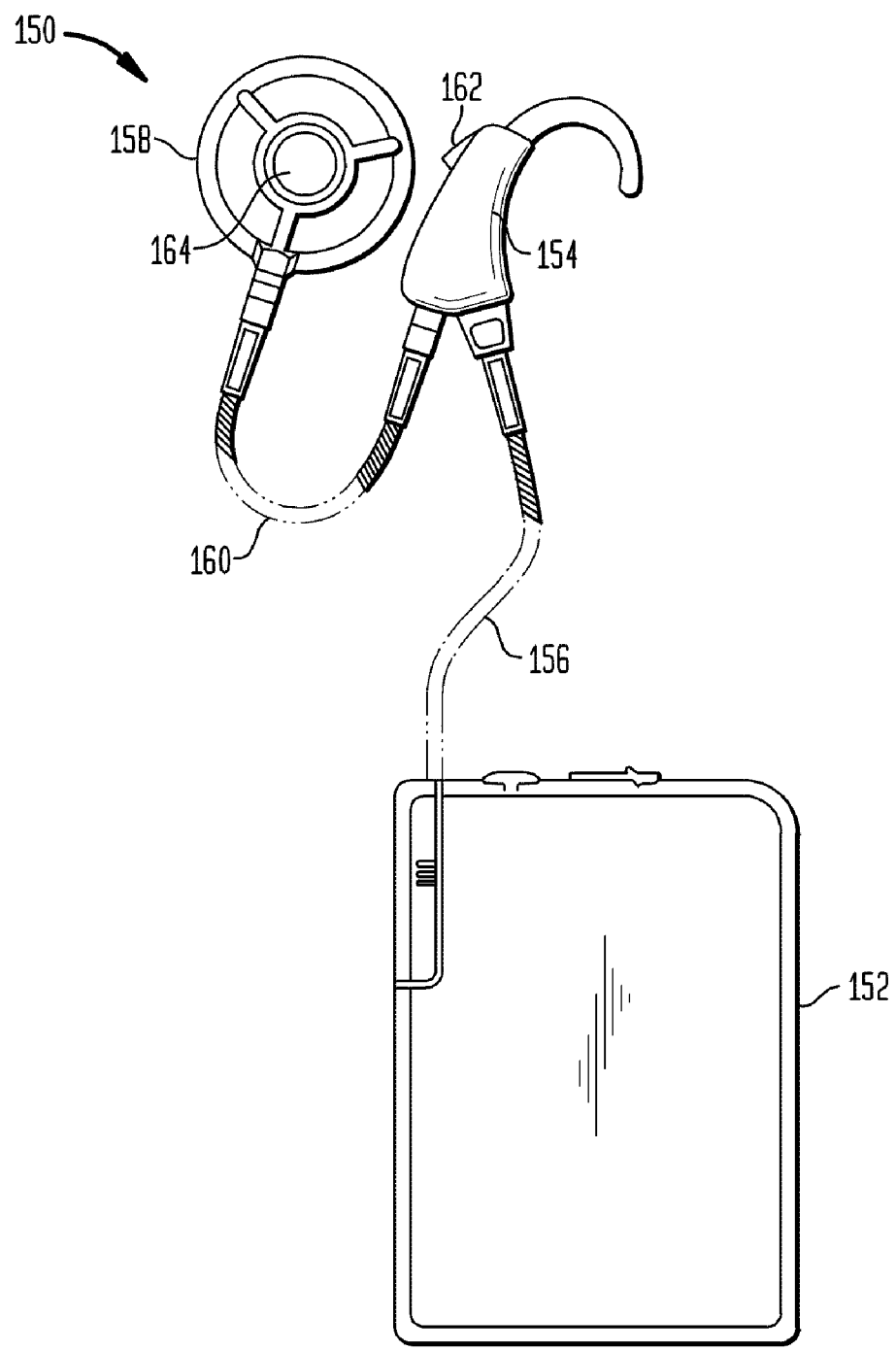
FIG. 1B is a schematic block diagram of an alternative embodiment of an exemplary acoustic prosthesis suitable for implementing embodiments of the present invention.

External assembly 142 of Cochlear™ implant system 100 may have different configurations and arrangements. FIG. 1B is a perspective view of one embodiment of external assembly 142, referred to as external assembly arrangement 150. In arrangement 150, a body-worn speech processing unit 152 is connected to a headset unit 154 with a first cable 206. Headset unit 154 is, in turn, connected to a transmitter coil 158 with a second cable 210.

In this exemplary embodiment, headset unit 154 comprises three audio pickup devices 162. In one embodiment, audio pickup devices 162 are microphones, although in alternative embodiments audio pickup devices 162 can be telecoils or other similar devices now or later developed. Each audio pickup device 162 detects and converts ambient sound into an electrical audio signal. The electrical audio signals are transmitted over cable 156 to speech processing unit 152, which contains appropriate speech processing circuitry to convert the electrical audio signals into electrical coded stimulation signals according to a particular speech processing strategy. The stimulation signals are transmitted via cable 156 from speech processing unit 152 to headset unit 154, and from headset unit 154 to external coil 158 via cable 160, for transmission over an RF link to implanted stimulator unit 126 (FIG. 1A).

Figure 2:
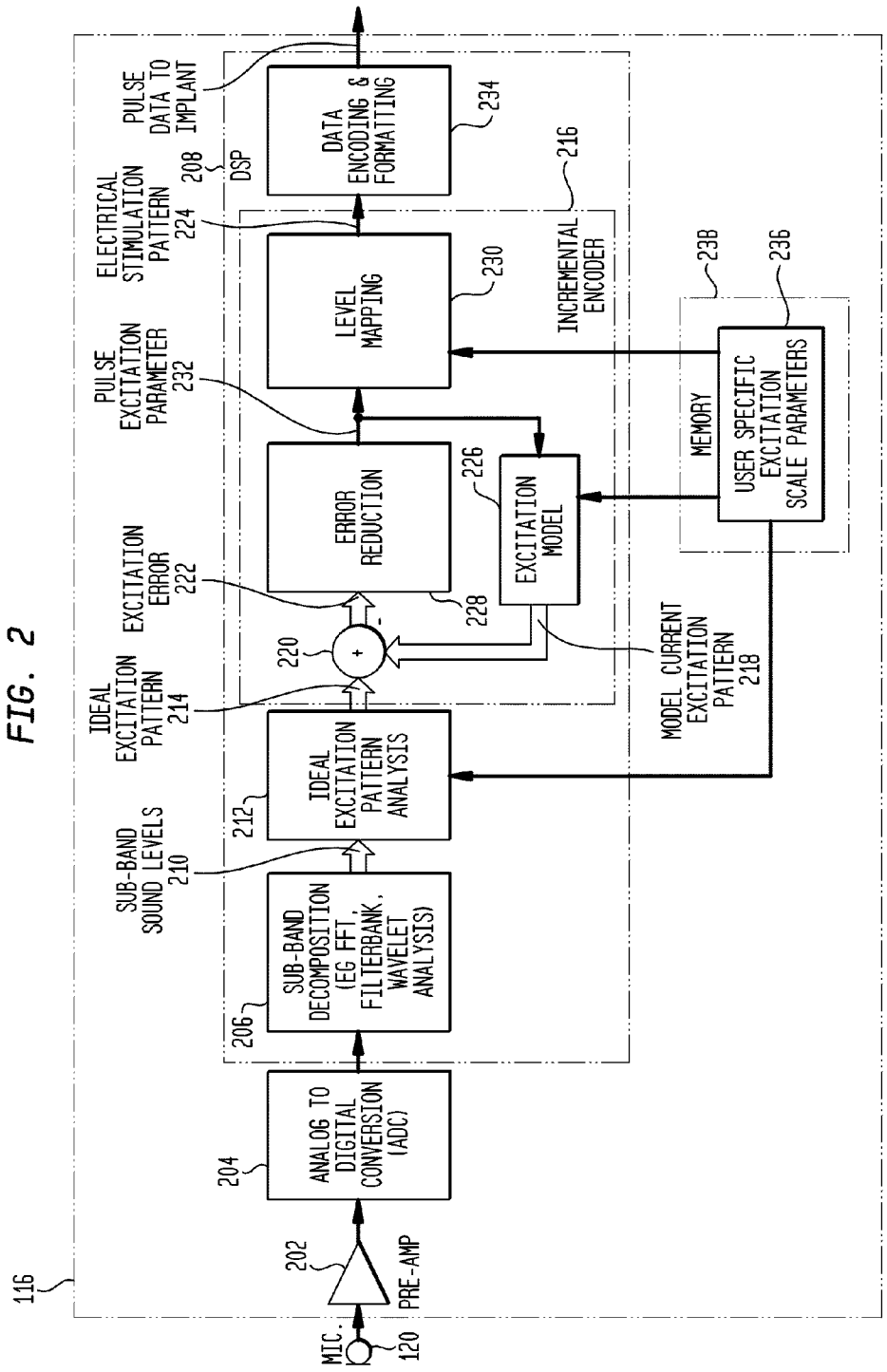
FIG. 2 is a functional block diagram of one embodiment of a speech processor of the present invention.

FIG. 2 is a functional block diagram of one embodiment of a portion of a speech processor of the present invention. Speech processor 116, as noted, receives an audio signal from microphone 120. Speech processor 116 comprises a pre-amplifier 202, an analog-to-digital converter (ADC) 204. Microphone 120 converts an acoustic input signal to an electrical signal, while pre-amplifier 202 typically includes an Automatic Gain Control (AGC) to amplify and control the level of the electrical signal generated by microphone 120. ADC 204 converts the electrical signal to a stream of digital samples for processing by the remaining components of speech processing unit 116.

As shown by the dashed box in FIG. 2, the remaining elements of speech processing unit 116 are implemented, in this example, in a digital signal processor (DSP) 208. Alternatively, such elements may be implemented in an application-specific integrated circuit (ASIC), or other hardware or combination of hardware and software, as deemed appropriate for the particular application.

DSP 208 first performs sub-band decomposition of the digitized audio signal at block 206. The operations performed at block 206 are collectively and generally referred to as a speech coding strategy. There are several speech coding strategies that may be used when converting the sound into an electrical stimulating signal. In one preferred embodiment, a low rate speech coding strategy. The present invention may be used in combination with any the following strategies: Continuous Interleaved Sampling (CIS), Spectral PEAK Extraction (SPEAK), Advanced Combination Encoders (ACE), Simultaneous Analog Stimulation (SAS), MPS, PPS, n-of-m and high resolution. SPEAK is a low rate strategy that may operate within the 250-500 Hz range. ACE is a combination of CIS and SPEAK. Examples of such speech strategies are described in U.S. Pat. No. 5,271,397, the entire contents and disclosures of which is hereby incorporated by reference. The present invention may also be used with other speech coding strategies now or later developed. The output of sub-band decomposition block 206 is a series of sub-band sound levels 210, as is well-known in the art.

Digital-Signal-Processor 208 comprises an ideal excitation pattern analyzer 212 that calculates an ideal excitation pattern 214 based on sub-band sound levels 210. Analyzer 212 may generate ideal excitation pattern 214 using a variety of methods now or later developed. In one embodiment, the spectral pattern of the energy in the sub-bands is converted into an into an excitation scale the spectral pattern of which defines ideal excitation pattern 214. On one embodiment, a power-law function is used for this transformation such that the logarithm of intensity is proportional to the logarithm of the excitation level. In such an embodiment, the constant of proportionality is the exponent of the power-law function. Other approaches now or later developed may be implemented in speech processor 116 to generate ideal excitation pattern 214 based on sub-ban sound levels 210.

DSP 208 also comprises an incremental encoder 216 and embodiment of which is illustrated in FIG. 2. Incremental encoder 216 generates stimulation pulses that incrementally builds a neural excitation pattern that accurately reflects a received sound. Specifically, incremental encoder 216 maintains and updates an estimation or model of a current or existing excitation pattern, referred to as existing excitation pattern 218) that takes into account the cumulative effect of all previously presented stimulus pulses presented at each electrode position. Existing excitation pattern 218 is subtracted from ideal excitation pattern 214 at 220 to generate an excitation error 222. Excitation error 222 is used to generate an electrical stimulus pattern 224 to make up the incremental difference in the excitation pattern. Existing excitation pattern 218 is then updated and the cycle is repeated.

As shown in FIG. 2, incremental encoder 216 comprises an excitation model 226 is used to generate existing excitation pattern 218. As will be described in detail below, excitation model 226 calculates an estimation or model of the total excitation by decay and effect of pulses. At block 228, incremental encoder 216 performs error reduction operations are performed to select pulse electrodes and pulse amplitudes to minimize a selected error criterion, as described in detail below. At level mapping block 230, incremental encoder 216 converts pulse excitation to electrical parameters to generate electrical stimulation pattern 224. The above and other aspects of incremental encoder 216 are described next below.

DSP 208 also comprises an output signal generator 234 that performs well-known data encoding and formatting operations on electrical stimulation pattern 214 to provide the stimulus pulse data to the implanted electrodes 134.

Excitation model 226 is implemented in incremental encoder 216 to provide information on the excitation evoked by each stimulus pulse, and on the total excitation as distributed across the cochlear. One feature of this model is an assumption of linear summation of excitation to evoke a perceived loudness.

The excitation patterns managed by incremental encoder 216 are essentially spatio-temporal distributions of excitation over the channels of cochlear implant 100. These excitation patterns are defined by a discrete time series of excitation values for each spatially-separated implant channel, forming an excitation vector at pulse time n:

$$\hat{E}[n] = \begin{bmatrix} e_{1,n} \\ e_{2,n} \\ \vdots \\ e_{C,n} \end{bmatrix}$$

where,
C=quantity of implant channels/electrodes,
n=pulse instance, and
$\hat{E}[n]$=Excitation Pattern at pulse interval n.

Each spatially-separated channel along electrode array 134 can be seen as having a separate excitation state causing a certain 'partial excitation'. These partial excitation quantities sum together to form the instantaneous overall loudness.

Excitation model 226 makes use of a number of assumptions regarding the way the overall excitation state evolves. First, each stimulus pulse is assumed to evoke a simple linear incremental contribution to the overall excitation state at the time of the stimulus pulse. The overall excitation state is then assumed to decay in time according to a constant exponential decay. The next excitation state across the cochlear is determined prior to application of a next successive stimulus pulse, by:

$$\hat{E}_{MODEL}[n+1] = e^{\frac{1}{f_p T_d}} \cdot (\hat{E}_{MODEL}[n] + \hat{E}_{PULSE}[n])$$

where, $\hat{E}_{Model}[n]$=Model of Current Neural Excitation Pattern at time interval n, $\hat{E}_{Model}[n+1]$=Model of Neural Excitation Pattern at time interval n+1, $\hat{E}_{Pulse}[n]$=Incremental Excitation Pattern, $f_p$=Pulse rate (Hz), and $T_d$=Decay time constant (seconds).

Figure 3A:
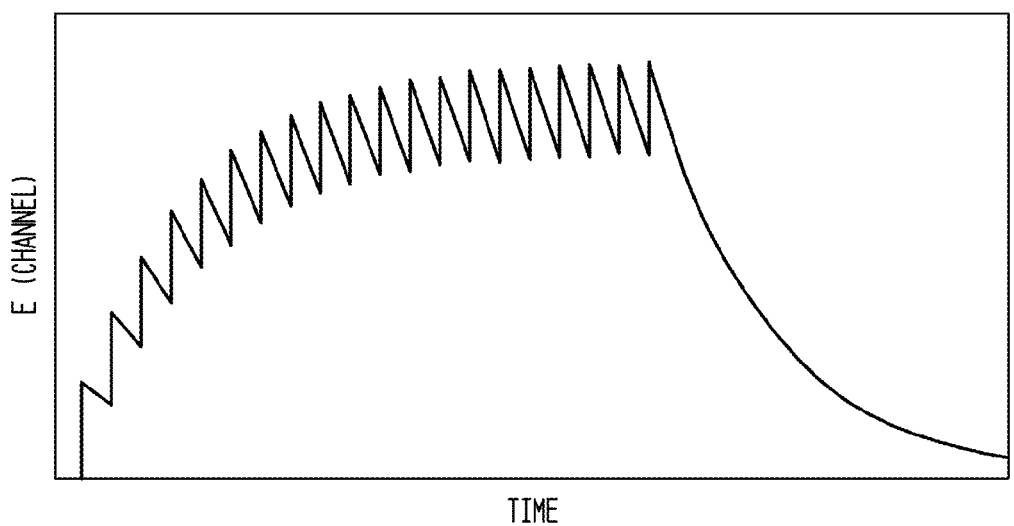
FIG. 3A is a depiction of a neural excitation pulse illustrating the incremental effect of each pulse and subsequent decay for a single channel with a modeled burst of constant pulse stimulation, followed by a period without pulses, in accordance with one embodiment of the present invention.

An example of the incremental effect of each pulse and subsequent decay for a single channel with a modeled burst of constant pulse stimulation, followed by a period without pulses, is illustrated in FIG. 3A. As noted, the excitation caused by a pulse on a given channel will likely 'spill over' or spread spatially, such that some excitation is also generated in adjacent channels. To allow for such spatial spreading, an excitation vector of a single pulse is determined by multiplying a single excitation amplitude by a set of constant linear weights across the implant channels. More specifically, the incremental excitation pattern, $E_{PULSE}[n]$, for a single pulse of instantaneous excitation amplitude P[n] on channel c[n], is calculated by:

$$\hat{E}_{PULSE}[n] = \hat{W}_S \times \hat{P}_c[n]$$

where:

$$\hat{W}_S = \begin{bmatrix} w_{11} & \cdots & w_{1C} \\ \vdots & \ddots & \vdots \\ w_{C1} & \cdots & w_{CC} \end{bmatrix},$$

$w_{ij}$=weight for channel i from pulse on channel j $$\hat{P}_c[n] = \begin{bmatrix} p_1 \\ \vdots \\ p_C \end{bmatrix}, p_i = 0 \text{ except } p_{c[n]} = P[n]$$

Figure 3B:
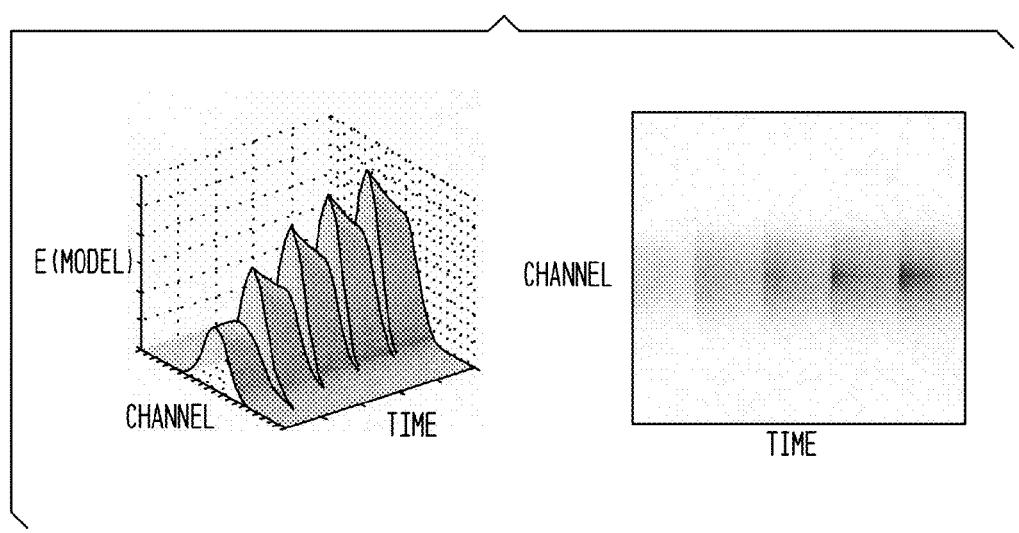
FIG. 3B is an illustration of an example of the general effect of broad spatial spreading weights on the modeled overall excitation pattern generated by a sequence of five pulses on a single channel, in accordance with one embodiment of the present invention.

In the special case of no spatial spreading, the spatial weights Ws becomes an identity matrix. An example of the general effect of broad spatial spreading weights on the modeled overall excitation pattern generated by a sequence of five pulses on a single channel is depicted in FIG. 3B.

Error reduction 228 locates electrode e[n] and amplitude P[n] to minimize an error criterion, an embodiment of which is described herein. As shown in FIG. 2, the excitation error $\hat{E}_{ERROR}[n]$ is calculated as the difference between the current ideal excitation state $\hat{E}_{IDEAL}[n]$ as generated by excitation pattern analysis 212 and the current model excitation state $\hat{E}_{MODEL}[n]$ 218:

$$\hat{E}_{ERROR}[n] = \hat{E}_{IDEAL}[n] - \hat{E}_{MODEL}[n]$$

Figure 4:
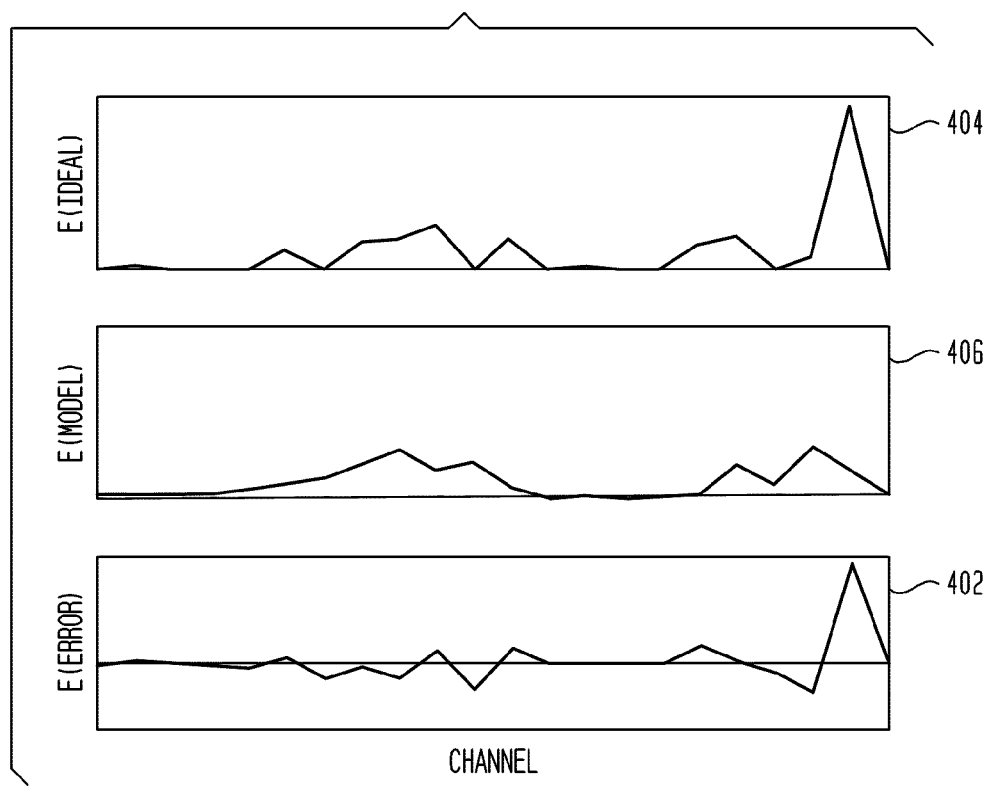
FIG. 4 depicts plots of an exemplary error excitation vector derived from an ideal excitation vector and a model current excitation vector, in accordance with one embodiment of the present invention.

FIG. 4 depicts plots of an exemplary error excitation vector 402 derived from an ideal excitation vector 404 and a model current excitation vector 406.

The objective of error reduction process 228 is to optimize the excitation produced by the implant by minimizing the error in the excitation. This optimization process usually operates to select the parameters of a pulse as defined by the pulse vector, Pc, so that a model error criterion is minimized:

$$\text{General Error Criterion: } Z_{ERROR}(c, P) = \left\| \hat{E}_{ERROR}[n] - \hat{W}_S \times \hat{P}_c \frac{\hat{E}_{PULSE}}{} \right\|_N$$

where $Z_{ERROR}$=a measure of the total, mean or mean square error in the proposed excitation state once the pulse vector Pc is applied. In the special case of no spatial spreading and an identity matrix Ws, the optimization task is typically reduced to placing a pulse on the channel with the largest error.

As noted, excitation model 226 provides information on the excitation evoked by each pulse, and on the total excitation as distributed across the cochlear. A central feature of this model is an assumption of linear summation of excitation to form a given loudness. Each spatially separated channel along implanted electrode 134 can be seen as having a separate excitation state causing a certain 'partial excitation'. These partial excitation quantities sum together to form the instantaneous overall loudness.

Figure 5:
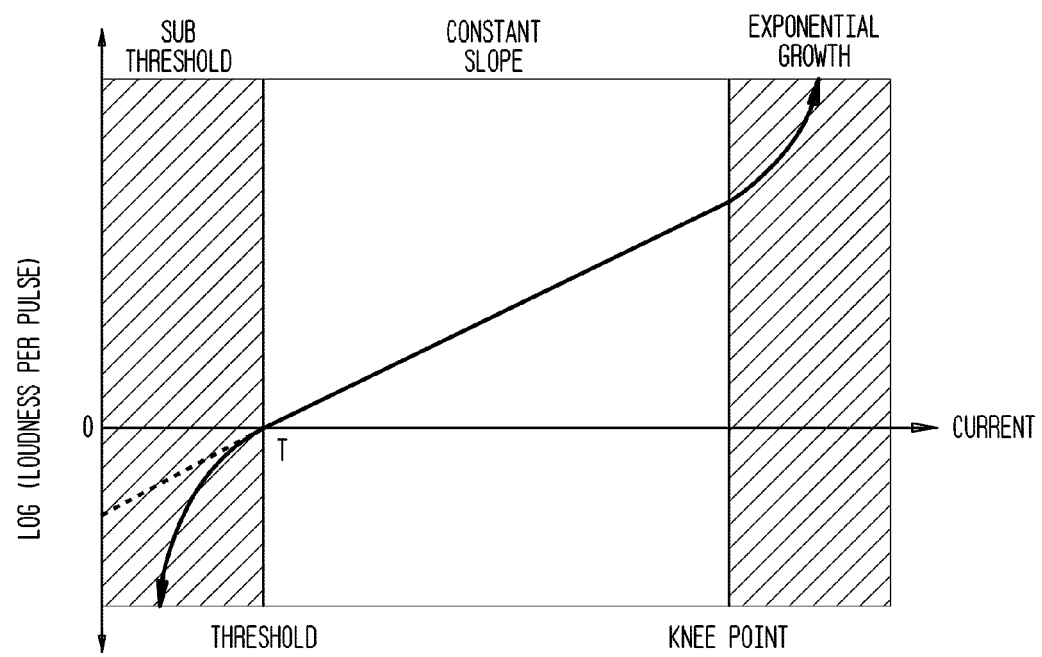
FIG. 5 is an illustration of a Log Excitation per Pulse (LEP) scale, in accordance with one embodiment of the present invention.

To quantify the excitation evoked by each electrical pulse, one must first determine how the excitation changes with the pulse parameters which may be varied. In one embodiment, only pulse current is varied in accordance with a Log Excitation per Pulse (LEP) scale, an embodiment of which is depicted in FIG. 5.

The LEP scale can be constructed by measuring each electrode for the pulse current levels required to balance the loudness of constant pulse trains of different rates. By an assumption of linear excitation summation, a factor change in rate will cause the same factor change in excitation. Thus by balancing loudness as a measure of excitation for different pulse rates, the current levels required to cause commensurate excitation differences can be found.

Note that the LEP relationship is dominated by a constant slope, although the loudness grows supra-exponentially beyond a certain knee point current level. Also note that the graph in FIG. 3A arbitrarily depicts LEP=0 for the traditional 'threshold' condition; that is, disappearance of loudness for a constant maximum rate pulse train of the given current level. The true threshold current level for an excitation effect per pulse in terms of the excitation model is likely to be lower.

In one embodiment, it was observed that while the threshold or offset current level does vary between electrodes, the slope of the linear region of the LEP scale is constant across electrodes. The linear region also generally spans around 6 'doublings' of the LEP scale (LEP=0 to LEP=6). This linear section of the relationship is therefore described by:

$$CL = C_n + S \times LEP$$

where,

CL is the current level, $C_n$ is the offset current level for electrode n,

S is the slope of the line in units of current level per LEP, and

LEP is the excitation desired.

Note that a mapping must typically be performed between the excitation pattern levels analysed at the input typically in units of acoustic level or intensity (in dB) to units of excitation (in LEP). In this example, it is assumed that the acoustic level relates linearly to the desired excitation, based on a simple conversion parameter D. Typical values of D would be 10 or 12 dB per LEP doubling.

Figure 6C:
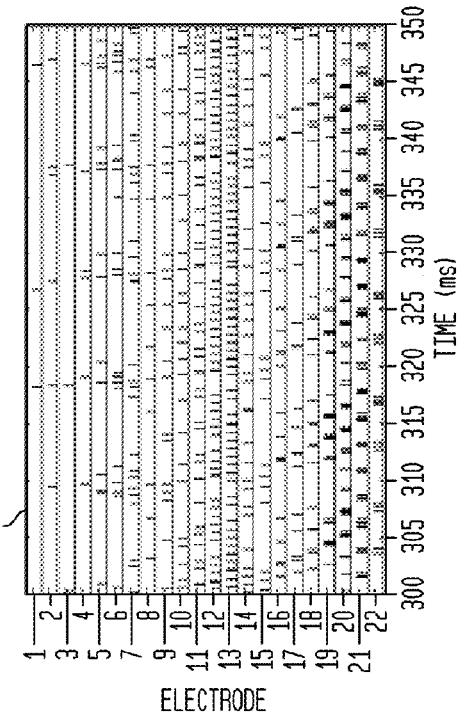
FIG. 6C is an illustration of an electrical stimulation pattern corresponding to the ideal excitation pattern illustrated in FIG. 6A and the model current excitation pattern illustrated in FIG. 6B, in accordance with one embodiment of the present invention.
Figure 6A:
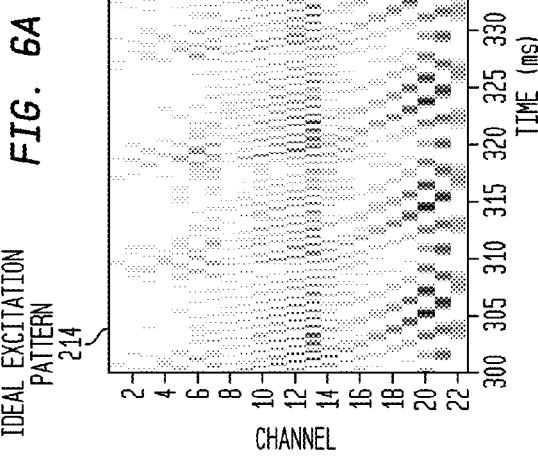
FIG. 6A is an illustration of an ideal excitation pattern in accordance with one embodiment of the present invention.
Figure 6B:
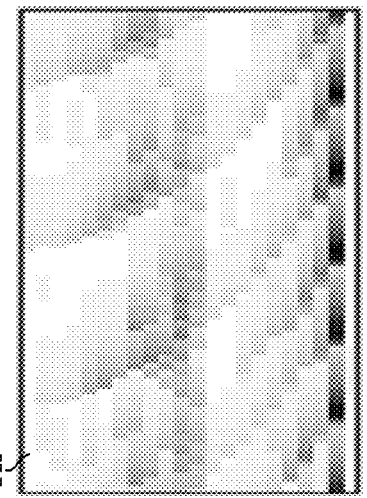
FIG. 6B is an illustration of a model current excitation pattern corresponding to the ideal excitation pattern illustrated in FIG. 6A, in accordance with one embodiment of the present invention.

FIG. 6A is an illustration of an ideal excitation pattern 214 in accordance with one embodiment of the present invention. A corresponding model current excitation pattern 218 is illustrated in FIG. 6B is an illustration of a model current excitation pattern generated by one embodiment of incremental encoder 216 of the present invention. FIG. 6C is an illustration of the resulting electrical stimulation pattern 224 generated by one embodiment of incremental encoder 216 of the present invention.

Figure 7B:
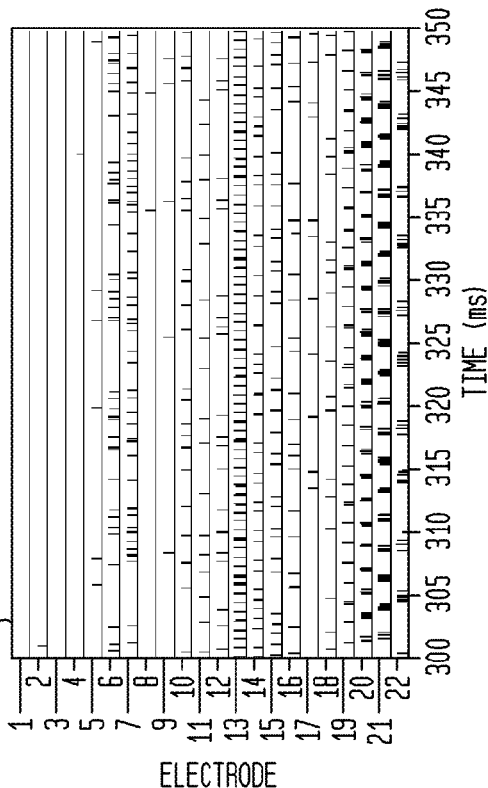
FIG. 7B is an illustration of an electrical stimulation pattern corresponding to the ideal excitation pattern illustrated in FIG. 7A, in accordance with one embodiment of the present invention.
Figure 7A:
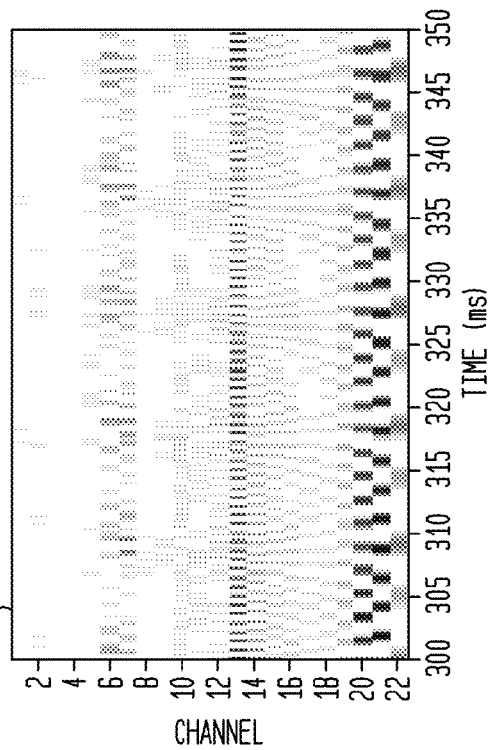
FIG. 7A is an illustration of an ideal excitation pattern in accordance with one embodiment of the present invention.
Figure 8A:
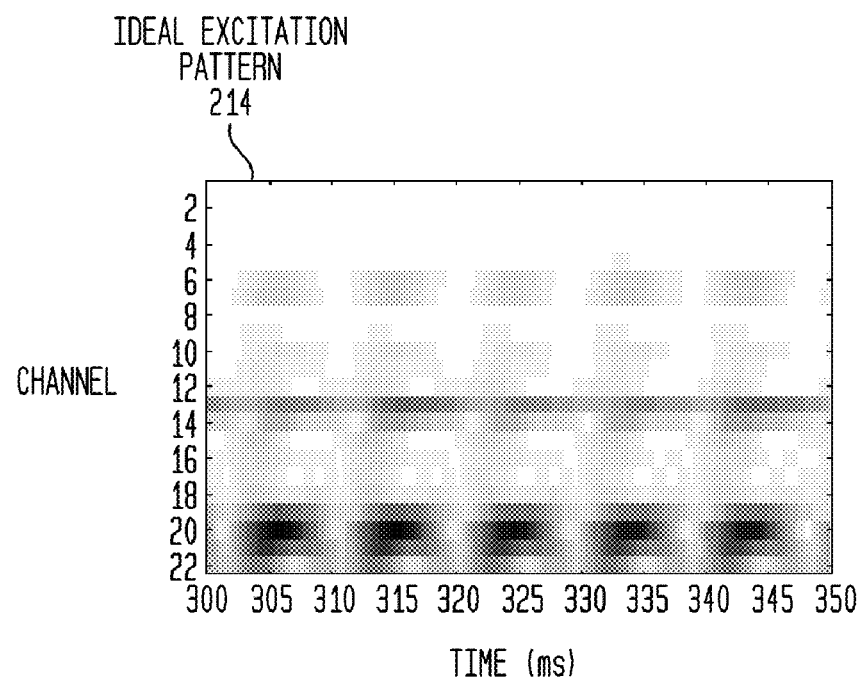
FIG. 8A is an illustration of an ideal excitation pattern in accordance with one embodiment of the present invention.
Figure 8B:
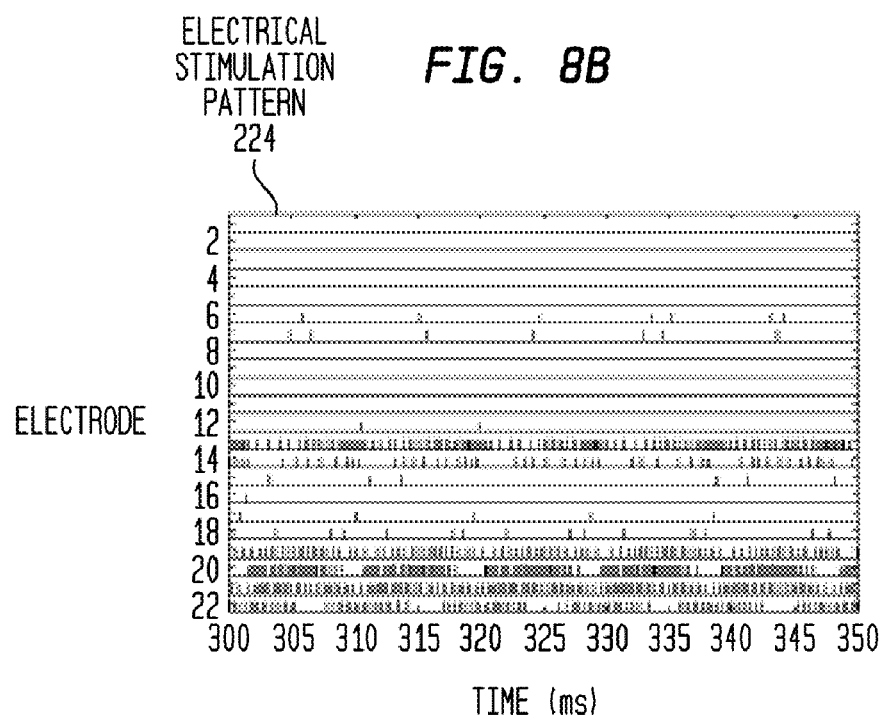
FIG. 8B is an illustration of an electrical stimulation pattern corresponding to the ideal excitation pattern illustrated in FIG. 8A, in accordance with one embodiment of the present invention.

As noted, the present invention can be implemented in conjunction with any speech strategy now or later developed. FIGS. 7A and 8A are illustrations of an ideal excitation pattern 214 generated in accordance with other speech strategies, while FIGS. 7B and 8B are the corresponding electrical stimulation patterns 224 corresponding to the ideal excitation patterns illustrated in FIGS. 7A and 8A, respectively, in accordance with one embodiment of the present invention.

Figure 9:
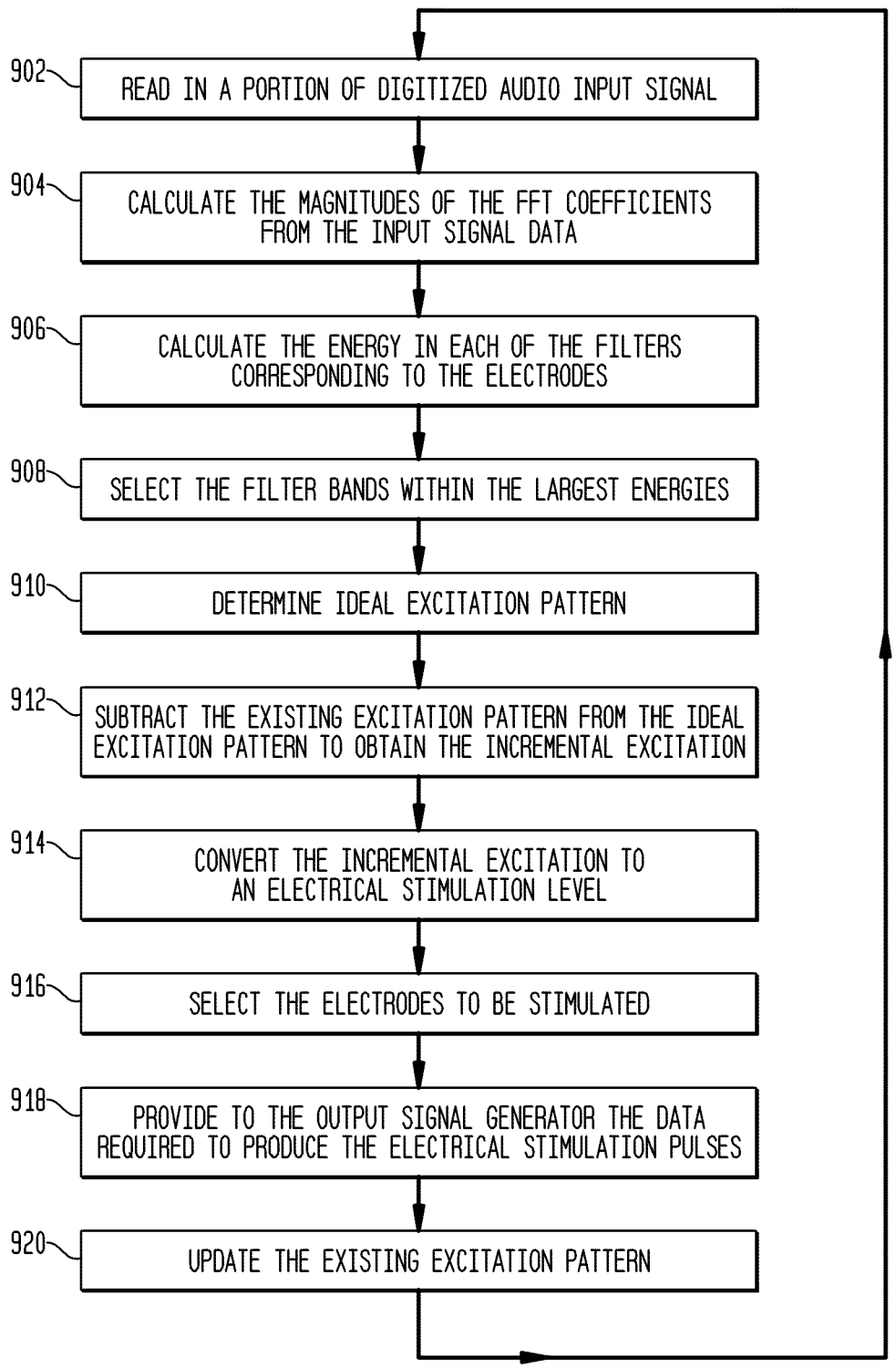
FIG. 9 is a flowchart of the operations performed in one embodiment of the present invention.

FIG. 9 is a flowchart of the operations performed in one embodiment of the present invention performed in a DSP implementing the above-noted SPEAK speech strategy. At block 902 a window of data is read from the input audio signal. For example, in one embodiment, 128 consecutive samples of audio data are read. At block 904, the magnitudes of the FFT coefficients from the window of input data are calculated. At block 906, the energy in each of the filters corresponding to the electrodes is calculated, for example, by adding together the magnitudes of the signal in each frequency band.

At block 908, the filter bands within the largest energies are selected. In one embodiment, six (6) or more spectral maxima are chosen. At block 910 the energies are converted into an excitation scale. This spectral pattern defines ideal excitation pattern 214. Typically, a power-law function is used for this transformation such that the logarithm of intensity is proportional to the logarithm of the excitation level. The constant of proportionality is the exponent of the power-law function.

At block 912, the existing excitation pattern is subtracted from the ideal excitation pattern to obtain the required incremental excitation. The incremental excitation is converted to an electrical stimulation level at block 914. This calculation is similar to the inverse of step 910, but the exponent of the power law function is greater for the electrical stimulation than for acoustic signals. It should be appreciated that this calculation is performed differently for each electrode, depending on the measured threshold and comfortable stimulation levels.

At block 916, the electrodes to be stimulated are selected, and at block 918 the output signal generator 234 is fed the data required to produce the electrical stimulation pulses. At block 920, the existing excitation pattern is updated by adding the contributions of the new stimulation pulses that have just been generated, and multiplying by a factor less than one. This factor represents the decay of the existing excitation of the neural system over the time internal between one set of stimuli and the next.

Various parameters need to be determined experimentally to make the incremental stimulation process work effectively. First, the conversions from acoustic energy to excitation and excitation to electrical stimulation current need to be determined accurately so that the subtraction of the existing excitation from the ideal excitation results in the appropriate incremental stimulation levels. As indicated above, the exponents for the conversion between excitation and electric current level needs to be determined for individual electrodes using measured threshold and comfortable levels or some similar loudness scaling or estimation procedure.

Second, the value for the factor representing the decay of existing excitation needs to be determined. The time constants for decay of existing excitation may be estimated from loudness scaling or estimation procedure. The time constants for decay of existing excitation may be estimated from loudness balancing of stimuli with different pulse rates or different inter-pulse intervals.

Third, the spread of excitation need to be estimated to allow for the excitation of neural elements by more than one electrode in the array. The spread of excitation can be estimated from masking experiments, as is well known in the art.

User-specific excitation scale parameters 236 are stored in programmable memory 238 to store patient-specific parameters, the processor programs, and intermediate results in calculating the excitation and stimulus patterns.

In the embodiments described above, the electrodes chosen for stimulation at block 916 will likely be the ones corresponding to the bands within maximum energy in block 908 according to the SPEAK strategy. However, the stimulation levels applied will be smaller than those that would have been applied without the incremental stimulation process, and there may be no need for stimulation at all on some electrodes if the acoustic intensity is falling faster than the existing excitation pattern or if there is substantial overlap of the excitation from adjacent electrodes.

If the excitation produced by a single stimulus pulse spreads substantially to adjacent electrodes, a more accurate approximation to the ideal excitation function will be produced by choosing only one electrode to stimulate at block 916, and then cycling through the operations at blocks 912-916 several times before returning to block 902. The additional cycling process will help avoid unnecessary stimulation of electrodes with substantially overlapping excitation functions.

It should be appreciated that Incremental encoder 216 can be used with any cochlear implant sound coding scheme now or later developed that calculates an ideal spatial excitation pattern. This includes all speech coding schemes including schemes based on non-simultaneous pulsatile stimulation. In alternative embodiments, incremental encoder 216 can be used in connection with analog and simultaneous pulsatile stimulation schemes, given sufficient data to be able to calculate the spread of neural excitation for any arbitrary electrical stimulus configuration.

As noted, the present invention takes into account all previous stimulus pulses on the electrode array. The present invention inherently compensates for the finite spatial extent of stimulation from individual electrodes, as well as for the temporal integration that takes place along the neural pathway. This is in contrast to conventional sound processors which calculate ideal excitation patterns which represent the spectral content of the signal and/or the variation in amplitude of bandpass-filtered components of the signals. These excitation patterns are then presented to the neural system by stimulating each electrode with the corresponding part of the excitation pattern. Then, a new excitation pattern is calculated and a completely new stimulation pattern is presented without regard to the potential spatial spread of stimulation from individual electrodes or the temporal integration that takes place in the auditory system.

Another advantage is that one or more stimulation pulses may be generated at selected places along the electrode array. Thus, a high rate, low charge per pulse stimulation pattern may be generated to insure each stimulation pulse is delivered to the most effective location in the cochlear while utilizing the full range of capabilities of stimulator unit 124.

The above and other features of the present invention are described in "An Incremental Excitation Scale For Cochlear Implants," by Peter J. Blamey, Bonar Dickson and Lois M. Grant, Acoustics Research Letters Online, vol. 5, No. 2, Mar.

1, 2004, the entire contents of which are hereby incorporated by reference herein in its entirety.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A hearing prosthesis implantable in a recipient and configured to receive a sound, comprising:
   an incremental encoder configured to generate a plurality of incremental excitation patterns each based on an effect of previously generated incremental excitation patterns on the recipient's auditory nerve,
      such that the incremental excitation patterns collectively and incrementally build a neural excitation on the auditory nerve that causes perception of the received sound, and
      such that, for a given one of the electrodes, the corresponding incremental excitation pattern is configured to compensate for at least one of spatial spreading of excitation from adjacent electrodes and temporal integration occurring along a corresponding neural pathway; and
   an output signal generator configured to convert the excitation patterns to patterns of stimulation pulses for delivery to the auditory nerve.

2. The prosthesis of claim 1, further comprising:
   a modeler configured to calculate a neural excitation existing on the auditory nerve at least partially based on at least one of the spatial spreading and the temporal integration; and
   wherein the encoder is further configured to determine a difference between an ideal excitation pattern representing the received sound and the calculated neural excitation pattern existing on the nerve, wherein the difference is used to generate the successive incremental excitation patterns.

3. The prosthesis of claim 2, wherein the modeler is further configured to calculate the neural excitation existing on the nerve at least partially based on a proximity effect of one or more previously generated excitation patterns.

4. The prosthesis of claim 2, wherein the modeler is further configured to calculate the neural excitation existing on the nerve at least partially based on a decay effect from one or more previously generated excitation patterns.

5. A hearing prosthesis implantable in a recipient and configured to receive a sound, comprising:
   an incremental encoder configured to generate a plurality of incremental excitation patterns each based on an effect of previously generated incremental excitation patterns on the recipient's auditory nerve such that the plurality of incremental excitation patterns collectively and incrementally build a neural excitation on the auditory nerve that causes perception of the received sound; and
   wherein the incremental encoder comprises:
   a modeler configured to calculate a neural excitation existing on the auditory nerve; and
   wherein the encoder is further configured to determine a difference between an ideal excitation pattern representing the received sound and the calculated neural excitation pattern existing on the nerve, wherein the difference is used to generate the successive incremental excitation patterns.

6. The prosthesis of claim 5, wherein the modeler is further configured to calculate the neural excitation existing on the nerve at least partially based on a spatial effect in the auditory nerve.

7. The prosthesis of claim 6, wherein the modeler is further configured to calculate the neural excitation existing on the nerve at least partially based on a proximity effect of one or more previously generated excitation patterns.

8. The prosthesis of claim 5, wherein the modeler is further configured to calculate the neural excitation existing on the nerve at least partially based on a temporal effect in the auditory nerve.

9. The prosthesis of claim 8, wherein the modeler is further configured to calculate the neural excitation existing on the nerve at least partially based on an accumulation effect from one or more previously generated excitation patterns.

10. The prosthesis of claim 8, wherein the modeler is further configured to calculate the neural excitation existing on the nerve at least partially based on a decay effect from one or more previously generated excitation patterns.

11. The prosthesis of claim 5 wherein the incremental encoder comprises:
    an error reducer configured to modify an incrementally generated excitation pattern based on the difference so as to minimize selected error criterion.

12. The prosthesis of claim 5, further comprising:
    a programmable memory configured to store the existing excitation pattern.

13. The prosthesis of claim 5, further comprising:
    an output signal generator configured to convert the excitation patterns to patterns of stimulation pulses for delivery to the auditory nerve.

14. A computer readable medium comprising a computer program which, when executed by a speech processor of a hearing prosthesis implanted in a recipient, implements a method for converting a received sound into a plurality of incremental excitation patterns, the method comprising:
    calculating a neural excitation currently existing on the recipient's auditory nerve; and
    determining a difference between an ideal excitation pattern representing the received sound and the calculated neural excitation existing on the nerve;
    generating successive incremental excitation patterns at least partially based on the difference.

15. The computer readable medium of claim 14, wherein the method further comprises:
    utilizing the difference to modify the incremental excitation pattern so as to minimize selected error criterion based.

16. The computer readable medium of claim 15, wherein hearing prosthesis comprises a plurality of stimulation channels, and wherein the method further comprises:
    selecting stimulation channels and associated pulse amplitudes of the incremental excitation pattern.

17. The computer readable medium of claim 14, wherein the method further comprises:
    converting the incremental excitation pattern into electrical stimulation levels used to generate stimulation pulses for delivery to the auditory nerve.

18. The computer readable medium of claim 14, wherein calculating the neural excitation existing on the nerve further comprises:

calculating the neural excitation existing on the nerve at least partially based on a spatial effect in the auditory nerve.

19. The computer readable medium of claim 18, further comprising:
calculating the neural excitation existing on the nerve using a proximity effect from one or more previously generated incremental excitation patterns.

20. The computer readable medium of claim 14, wherein calculating the neural excitation existing on the nerve further comprises:
calculating the neural excitation existing on the nerve at least partially based on a temporal effect in the auditory nerve.

21. The computer readable medium of claim 20, further comprising:
calculating the neural excitation existing on the nerve at least partially based on an accumulation effect from one or more previously generated excitation patterns.

22. The computer readable medium of claim 20, further comprising:
calculating the neural excitation existing on the nerve based at least partially on a decay effect from one or more previously generated excitation patterns.

23. The computer readable medium of claim 14, wherein the method further comprises:
storing said existing excitation pattern.

24. A speech processor for a hearing prosthesis at least partially implantable in a recipient and configured to receive an audio signal, comprising:
an incremental encoder configured to generate a plurality of incremental excitation patterns each based on an effect of previously generated incremental excitation patterns on the recipient's auditory nerve,
such that the incremental excitation patterns collectively and incrementally build a neural excitation on the auditory nerve that causes perception of the received sound; and
such that, for a given one of the electrodes, the corresponding incremental excitation pattern is configured to compensate for at least one of spatial spreading of excitation from adjacent electrodes and temporal integration occurring along a corresponding neural pathway.

25. A speech processor for a hearing prosthesis at least partially implantable in a recipient and configured to receive an audio signal, comprising:
an incremental encoder configured to generate a plurality of incremental excitation patterns each based on an effect of previously generated incremental excitation patterns on the recipient's auditory nerve such that the incremental excitation patterns collectively and incrementally build a neural excitation on the auditory nerve that causes perception of the received sound;
wherein the incremental encoder comprises:
a modeler configured to calculate a neural excitation existing on the auditory nerve;
wherein the encoder is further configured to determine a difference between an ideal excitation pattern representing the received sound and the calculated neural excitation pattern existing on the nerve, wherein the difference is used to generate the successive incremental excitation patterns.

26. The speech processor of claim 25, wherein the modeler is further configured to calculate the neural excitation existing on the nerve at least partially based on a spatial effect in the auditory nerve.

27. The speech processor of claim 26, wherein the modeler is further configured to calculate the neural excitation existing on the nerve at least partially based on a proximity effect of one or more previously generated excitation patterns.

28. The speech processor of claim 25, wherein the modeler is further configured to calculate the neural excitation existing on the nerve at least partially based on a temporal effect in the auditory nerve.

29. The speech processor of claim 28, wherein the modeler is further configured to calculate the neural excitation existing on the nerve at least partially based on an accumulation effect from one or more previously generated excitation patterns.

30. The speech processor of claim 28, wherein the modeler is further configured to calculate the neural excitation existing on the nerve at least partially based on a decay effect from one or more previously generated excitation patterns.

31. The speech processor of claim 24 wherein the incremental encoder comprises:
an error reducer configured to modify an incrementally generated excitation pattern based on the difference so as to minimize selected error criterion.

32. The speech processor of claim 25, further comprising:
a programmable memory configured to store the existing excitation pattern.

* * * * *